United States Patent [19]

Verplank

[11] 4,326,547
[45] Apr. 27, 1982

[54] TOOTH PROBE DEVICE

[76] Inventor: C. Michael Verplank, P.O. Box 564, Crested Butte, Colo. 81224

[21] Appl. No.: 203,250

[22] Filed: Nov. 3, 1980

[51] Int. Cl.³ ............................................. A61C 15/00
[52] U.S. Cl. ........................................ 132/89; 132/93
[58] Field of Search ................ 132/89, 90, 91, 93; 131/245

[56] References Cited

U.S. PATENT DOCUMENTS

| 407,362 | 7/1889 | Mason | 132/91 |
|---|---|---|---|
| 1,996,205 | 4/1935 | Jackson | 132/89 |
| 2,189,556 | 2/1940 | Younghusband | 131/245 |
| 2,304,281 | 12/1942 | Riley | 131/245 |
| 2,486,247 | 10/1949 | Berlin et al. | 131/245 |
| 2,648,341 | 8/1953 | Moll | 132/91 |
| 2,931,366 | 4/1960 | Siegel | 132/93 |
| 3,789,858 | 2/1974 | Pesce | 132/89 |
| 3,908,677 | 9/1975 | Beach | 132/91 |
| 3,930,059 | 12/1975 | Wells | 132/91 |
| 3,942,539 | 3/1976 | Corliss et al. | 132/91 |
| 4,135,528 | 1/1979 | Stark | 132/89 |

Primary Examiner—Paul J. Hirsch
Attorney, Agent, or Firm—J. William Wigert, Jr.

[57] ABSTRACT

A teeth-cleaning device includes a rod-shaped, small diameter strand about which is surrounded a softer, floss-type material. The rod-shaped material is of sufficient stiffness to allow it to be used to remove food particles lodged between teeth, but sufficiently flexible to allow the invention to be bent to conform to the contours of the teeth for removing plaque. The material is also resilient, i.e., non-deformable, so that it returns to its original shape once it is removed from between the teeth for ease of use.

8 Claims, 3 Drawing Figures

TOOTH PROBE DEVICE

BACKGROUND OF INVENTION

The present invention relates to a device for cleaning teeth, and in particular for a teeth-cleaning device which has improved handling characteristics.

It is well known that small diameter lengths of wood or other soft material are useful as probes or "picks" in the removal of food particles trapped between human teeth. The stiff nature of these materials, when such materials are of sufficiently large diameter, provides the rigidity necessary to withstand the pressure applied to the probe to dislodge the trapped food particle. However, toothpicks have a number of disadvantages. First, their stiffness and necessarily large diameter prevent them from being inserted into the narrower recesses between the teeth. Second, the area of the pick which is effective in cleaning the teeth is limited to the tip of the toothpick which is in contact with the teeth. Third, since they are rigid, they are not useful in scrubbing dental plaque from tooth surfaces, since they are unable to conform to the shape of the tooth.

It is also well known that dental floss has the proper abrasive texture and flexibility to effectively remove dental plaque from tooth surfaces. In addition, the string-like quality of dental floss coupled with its small diameter allow the floss to be positioned in narrow recesses and shaped to conform to the shape of the tooth, thus providing greater effective cleaning area. As a result, dental floss is more effective at cleaning dental plaque from teeth than is a toothpick.

However, in order to use dental floss a certain minimum level of dexterity is required. This minimum level is often lacking in children under the age of 12 thus often precluding these persons from using dental floss effectively. In addition, because dental floss is string-like, it cannot be used in the manner of a toothpick.

In U.S. Pat. No. 3,930,059, sections of ordinary dental floss are rigidized by thickening the floss with more of the same material it is made of or by reinforcing it by the application of a wax or plastic coating to render it resilient, firm, or rigid at periodic places along the roll of dental floss. These rigid portions act as a leader to guide the floss between the teeth and also to act as a pick. It also takes two hands to be properly manipulated.

This arrangement has several drawbacks, however. If the rigidized section is built up of more floss material or wax, it has little resiliency, and is deformable. This makes it difficult to use, for example, by a child. On the other hand, if a plastic material is used for this purpose, while it may be more resilient, it no longer has an exterior surface of a "floss" material. In other words, it is really a "pick" and not "floss."

SUMMARY OF THE INVENTION

It is therefore an object of the invention to provide a rod-shaped non-deformable tooth probe of small diameter, which is stiff yet resilient, and which, with a minimum level of dexterity, can be used to clean teeth with one hand.

Another object of the invention is to provide a teeth-cleaning device which has the cleaning capability of, but which is easier to use than, dental floss.

Yet another object of the invention is to provide a rod-shaped, small diameter, stiff yet resilient, non-deformable probe which is encased in a floss-like material, the total diameter of which is less than the spacing of a majority of crevices found in and between human teeth.

The improved teeth-cleaning device of the present invention includes a rod-shaped, small diameter strand about which is surrounded a softer, floss-type material. The rod shaped material is of sufficient stiffness to allow it to be used to remove food particles lodged between teeth, but sufficiently flexible to allow the invention to be bent to conform to the contours of the teeth for removing plaque. The material is also resilient, i.e., non-deformable, so that it returns to its original shape once it is removed from between the teeth for ease of use. The abrasive material may be secured to the rod shaped material by one of several methods which include extrusion, wrapping and coating.

The invention is thus a floss-like device that may be used in the manner of a toothpick but which has many of the benefits of dental floss.

BRIEF DESCRIPTION OF DRAWINGS

FIG. 2 is an enlarged view of another embodiment of the improved tooth probe of the present invention wherein the exterior surface is sprayed on.

FIG. 3 is an enlarged view of another embodiment of the present invention wherein the exterior floss surface is extruded on.

DESCRIPTION OF PREFERRED EMBODIMENTS

Figure 1:
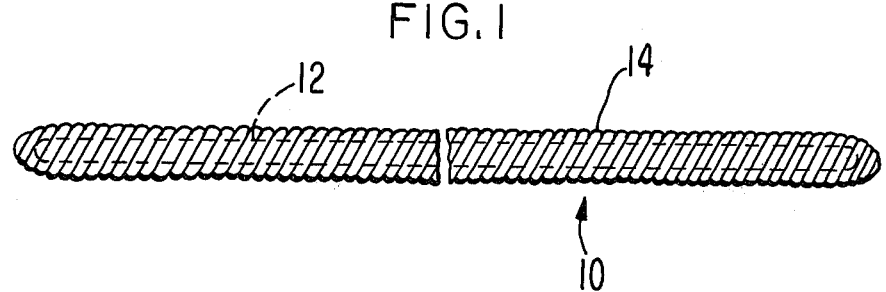
FIG. 1 is an enlarged view of the improved tooth probe of the present invention having a wrapped-on surface of floss.
Figure 2:
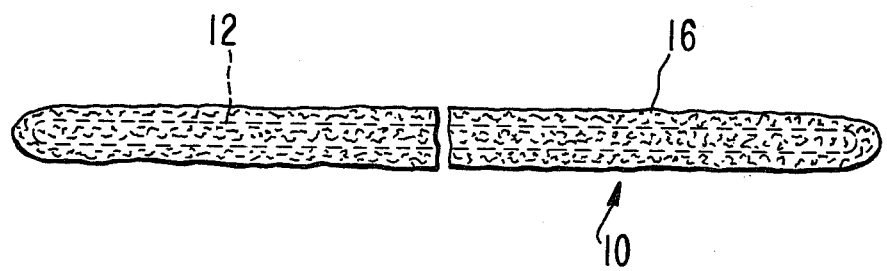
Figure 3:
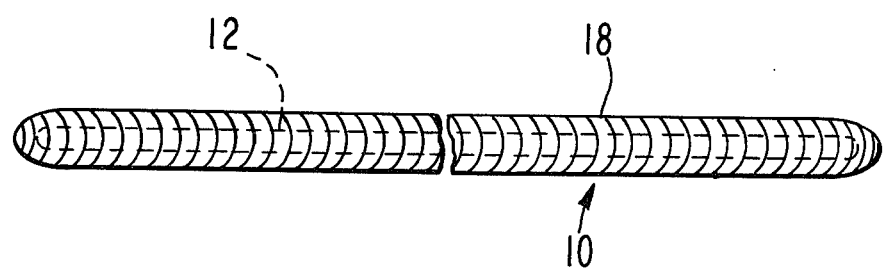

FIGS. 1, 2 and 3 show three embodiments of an improved tooth probe 10 in accordance with the present invention. In each embodiment there is provided a central core or strand 12. Strand 12 is made of a material which is stiff, but is also flexible and resilient and has the property that it is non-deformable. By the latter it is meant that if it is flexed, within limits, it will return to its original shape.

One example of a material suitable for the central strand 12 is spring steel wire, having a diameter of 0.012 inches or less. Other materials such as plastic can also be used provided they have the same rigid, resilient, non-deformable characteristics as spring steel.

The central strand 12 typically is several inches long. The length is selected so that it is easily held with one hand, but is not so long that it intrudes too far into the mouth when used. The central strand 12 is provided with an exterior of floss or floss-like material. The characteristics of this material is that it be sufficiently soft so as not to damage the teeth or gums, and yet sufficiently sturdy and/or abrasive to remove plaque from the teeth and food debris from between the teeth.

In FIG. 1 the central strand 12 is surrounded by a conventional thread of very small diameter floss 14. The thin thread of floss 14 may be wrapped or spun around the strand 12. If necessary, an adhesive may be used to maintain the floss in engagement with the strand 12 both along the length of strand 12 as well as at the ends thereof.

In FIG. 2 an outer surface of a floss-like material 16 is provided on the strand 12 by spraying it on the strand 12. Once again, a suitable adhesive may be first used on the strand 12 before the floss-like material is sprayed on.

This particular technique ensures a rougher, more abrasive surface but one which is still soft to teeth and gums.

In FIG. 3, the floss material 18 is extruded on the strand 12. Once again the material can be ordinary floss or it can also be other materials that have the same characteristics of softness and durability as floss.

Another way to form probe 10, not shown, is to insert the strand 12 within a pre-existing bag or enclosure made of floss.

The total diameter of the central strand 12 and the outer floss surface is comparable to ordinary floss presently available. This ensures that the tooth probe 10 can easily be inserted between the teeth. At the same time, due to the flexibility of the combination of the strand 12 and the outer floss material, the probe 10 is flexible enough to conform to the curvature of the teeth and gums. And, owing to the non-deformability of the strand 12, the tooth probe 10 can be pushed, by one hand, in various directions and in varying degrees of force, between the teeth and return to its original shape when withdrawn from the mouth. This greatly facilitates its use, particularly by children. An ideal length for probe 10 is 2¼ inches.

If it is desired, the tooth probe 10's outer floss surface may be coated with a coating of wax, as is available with conventional dental floss.

What is claimed is:

1. A dental probe comprising:
   an unsupported thin core strand having a generally uniform cross-section of a material which is stiff and flexible but returns to substantially its original shape when not stressed; and an outer sheath surrounding said core strand made of a material suitable for engaging teeth and gums.
2. A dental probe, as in claim 1, wherein the core strand is made of narrow gauge spring steel.
3. A dental probe as in claim 2 wherein said sheath is made of floss.
4. A dental probe as in claim 3 wherein said sheath comprises a thin thread of floss wrapped around said strand.
5. A dental probe as in claim 3 wherein said sheath is extruded on said strand.
6. A dental probe as in claim 3 wherein said sheath is sprayed on said strand.
7. A dental probe as in claim 3 wherein said strand fits within a floss bag.
8. A method of manufacturing a dental probe comprising the step of surrounding an unsupported thin, central rod having a generally uniform cross-section of a material which has the characteristics of being stiff and resilient but returns to substantially its original shape when not stressed, with an outer surface of floss.

* * * * *